US010201407B2

(12) United States Patent
Stevens et al.

(10) Patent No.: US 10,201,407 B2
(45) Date of Patent: *Feb. 12, 2019

(54) DEVICE AND METHOD FOR FACILITATING TOOTH CONTACT ADJUSTMENT USING A PRESSURE DEVICE

(71) Applicant: International Business Machines Corporation, Armonk, NY (US)

(72) Inventors: Mark B. Stevens, Austin, TX (US); John D. Wilson, League City, TX (US)

(73) Assignee: International Business Machines Corporation, Armonk, NY (US)

( * ) Notice: Subject to any disclaimer, the term of this patent is extended or adjusted under 35 U.S.C. 154(b) by 460 days.

This patent is subject to a terminal disclaimer.

(21) Appl. No.: 14/929,610

(22) Filed: Nov. 2, 2015

(65) Prior Publication Data
US 2017/0049544 A1 Feb. 23, 2017

Related U.S. Application Data

(63) Continuation of application No. 14/828,808, filed on Aug. 18, 2015.

(51) Int. Cl.
*G06F 17/50* (2006.01)
*A61B 5/00* (2006.01)
(Continued)

(52) U.S. Cl.
CPC ............ *A61C 19/05* (2013.01); *A61B 5/4547* (2013.01); *A61B 5/743* (2013.01); *A61B 5/7425* (2013.01);
(Continued)

(58) Field of Classification Search
CPC ......... A61C 19/05; G01L 1/205; G06T 17/00; G06T 2210/41; G06T 19/00;
(Continued)

(56) References Cited

U.S. PATENT DOCUMENTS 4,521,186 A * 6/1985 Wodlinger ............. A61C 19/05
433/71
5,340,309 A 8/1994 Robertson
(Continued)

FOREIGN PATENT DOCUMENTS

| WO | WO9701992 A1 | 1/1997 |
| WO | 2009006273 A2 | 1/2005 |
| WO | 2012090211 A1 | 7/2015 |

OTHER PUBLICATIONS

Lipomi et al., "Skin-like Pressure and Strain Sensors Based on Transparent Elastic Films of Carbon Nanotubes", Nature Nanotechnology, vol. 6, Dec. 2011, pp. 788-792.
(Continued)

*Primary Examiner* — Harshad R Patel
*Assistant Examiner* — Brandi N Hopkins
(74) *Attorney, Agent, or Firm* — Robert D. Bean

(57) ABSTRACT

A structure and method of visualizing and evaluating areas of tooth contact between upper and lower teeth when the upper and lower arches of a mouth are in a closed or occluded condition. The method includes performing a plurality of readings of tooth contacts, by a pressure sensing device, during a period of time and determining sensing properties of the tooth contacts based on the plurality of readings, wherein the sensing properties include one or more of: sequence of a first tooth contact relative to at least a second tooth contact, and pressure magnitude of the first tooth contact.

10 Claims, 7 Drawing Sheets

(51) Int. Cl.
*A61B 5/22* (2006.01)
*A61C 19/05* (2006.01)
*G01L 5/00* (2006.01)
*A61C 7/00* (2006.01)
*A61C 8/00* (2006.01)

(52) U.S. Cl.
CPC ............... *A61C 7/002* (2013.01); *A61C 8/00* (2013.01); *G01L 5/00* (2013.01); *A61B 2562/0285* (2013.01)

(58) Field of Classification Search
CPC . G06T 2219/008; A61B 5/228; A61B 5/0002; A61B 5/4542; A61B 5/682
See application file for complete search history.

(56) References Cited

U.S. PATENT DOCUMENTS

| | | | |
|---|---|---|---|
| 5,730,151 A * | 3/1998 | Summer | A61C 19/04 600/587 |
| 7,160,110 B2 | 1/2007 | Imgrund et al. | |
| 9,123,147 B2 * | 9/2015 | Barneoud | G06T 19/00 |
| 2003/0191507 A1 * | 10/2003 | Simmons | A61F 4/00 607/48 |
| 2005/0095562 A1 | 5/2005 | Sporbert et al. | |
| 2005/0069188 A1 | 12/2005 | Rubbert et al. | |
| 2008/0295850 A1 | 12/2008 | Lesniak | |
| 2016/0242692 A1 * | 8/2016 | McAuliffe | A61B 5/228 |
| 2016/0302901 A1 | 10/2016 | Brel et al. | |
| 2017/0265978 A1 * | 9/2017 | Borotto | A61C 19/05 |

OTHER PUBLICATIONS

Takei et al., "Nanowire Active-Matrix Circuitry for Low-Voltage Macroscale Artificial Skin", published online, Sep. 12, 2010, http://www.nature.com/nmat/journal/v9/n10/full/nmat2835.html, pp. 1-3.
Pending U.S. Appl. No. 14/828,808, filed Aug. 18, 2015, entitled: "Facilitating Tooth Contact Adjustment", 33 pages.
IBM: List of IBM Patents or Patent Applications Treated As Related (Appendix P), Jan. 8, 2018, pp. 1-2.
Stevens et al., Pending U.S. Appl. No. 14/828,808, filed Aug. 18, 2015, titled "Facilitating Tooth Contact Adjustment," pp. 1-33.

* cited by examiner

600

Performing a plurality of readings of tooth contacts
604

Determining sensing properties of the tooth contacts
608

Displaying a graphical representation of the sensing properties of the tooth contacts
616

10,201,407 B2

DEVICE AND METHOD FOR FACILITATING TOOTH CONTACT ADJUSTMENT USING A PRESSURE DEVICE

BACKGROUND

Embodiments of the present invention relate generally to the fields of dentistry and orthodontics, and more particularly to a structure and method of visualizing and evaluating areas of tooth contact between upper and lower teeth when the upper and lower arches of a mouth are in a closed or occluded condition.

When a dentist or an orthodontist performs a procedure such as aligning teeth with braces, implanting teeth, or installing crowns, the procedure may typically involve analyzing how teeth in one arch mate with teeth in the opposing arch when the jaws clench. If a particular tooth has a cusp that extends more than what is desirable for an ideal bite, it may strike an opposing tooth early, thereby throwing off the bite. Unless corrected, this can eventually lead to conditions such as tooth pain, temperature sensitivity, temporomandibular disorders (TMD), or damaged teeth.

SUMMARY

According to an embodiment, a method of visualizing tooth contact properties is provided. The method may include performing a plurality of readings of tooth contacts, by a pressure sensing device, during a period of time. The method may also include determining sensing properties of the tooth contacts, based on the plurality of readings, wherein the sensing properties include one or more of: sequence of a first tooth contact relative to at least a second tooth contact, and pressure magnitude of the first tooth contact.

According to another embodiment, a method of visualizing tooth contact properties is provided. The method may include placing a pressure sensing device between an upper and a lower jaw of a mouth, conforming one face of the pressure sensing device to an occlusal surface of a first tooth, and conforming another face of the pressure sensing device to occlusal surface of an opposing second tooth. The method may also include performing a plurality of readings of contacts between the first tooth and the second tooth, by the pressure sensing device, during a period of time. The method may also include determining sensing properties of the contacts, based on the plurality of readings, wherein the sensing properties include one or more of: sequence of a first tooth contact relative to at least a second tooth contact, and pressure magnitude of the first tooth contact.

According to another embodiment, a device for visualizing teeth contact properties is provided. The device may include a pressure sensing device comprising a film element deformable by mechanical pressure configured for placement between an upper and a lower jaw of a mouth, wherein the film element is shaped to be in contact with one or more teeth in the mouth, the film element comprising a plurality of point of contact sensors and a plurality of pressure magnitude sensors. The device may also include a processor in communication with the pressure sensing device so as to receive a plurality readings by the pressure sensing device.

BRIEF DESCRIPTION OF THE DRAWINGS

The following detailed description, given by way of example and not intended to limit the invention solely thereto, will best be appreciated in conjunction with the accompanying drawings, in which not all structures may be shown.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
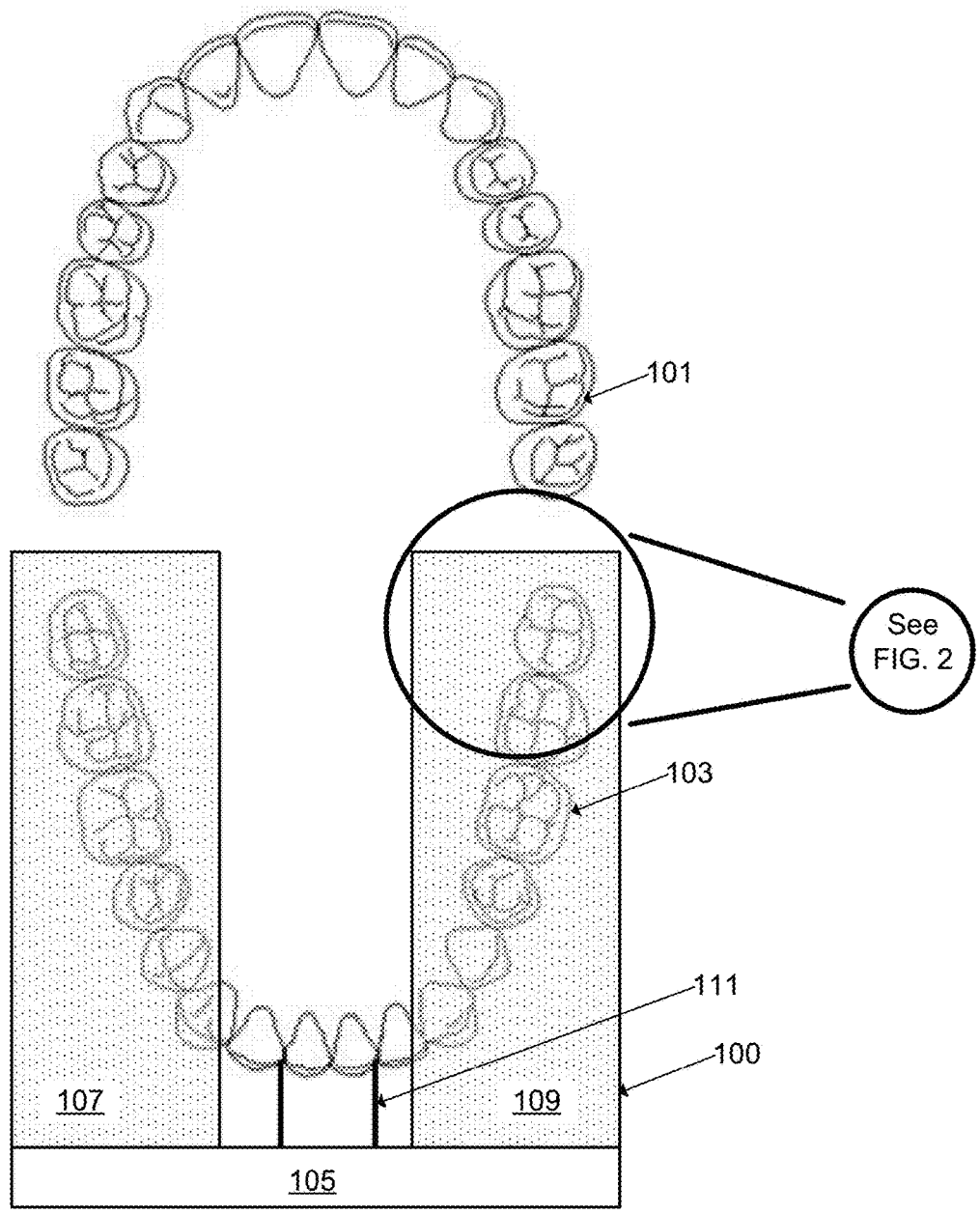
FIG. 1 illustrates a plan view of a pressure sensing device placed on teeth of a lower arch of a mouth, according to an embodiment of the invention.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art.

In the following description, numerous specific details are set forth, such as particular structures, components, materials, dimensions, processing steps, and techniques, in order to provide a thorough understanding of the present invention. However, it will be appreciated by one of ordinary skill of the art that the invention may be practiced without these specific details. In other instances, well-known structures or processing steps have not been described in detail in order to avoid obscuring the invention. It will be understood that when an element as a layer, region, or substrate is referred to as being "on" or "over" another element, it can be directly on the other element or intervening elements may also be present. In contrast, when an element is referred to as being "directly on" or "directly" over another element, there are no intervening elements present. It will also be understood that when an element is referred to as being "beneath," "below," or "under" another element, it can be directly beneath or under the other element, or intervening elements may be present. In contrast, when an element is referred to as being "directly beneath" or "directly under" another element, there are no intervening elements present.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

When a dentist or an orthodontist performs a procedure such as aligning teeth with braces, implanting teeth, or installing crowns, the procedure may typically involve analyzing how teeth in one arch mate with teeth in the opposing arch when the jaws clench in a closed or occluded condition. If a particular tooth has a cusp that extends more than what is desirable for an ideal bite, it may strike an opposing tooth early, thereby throwing off the bite. Unless corrected, this can eventually lead to conditions such as tooth pain, temperature sensitivity, temporomandibular disorders (TMD), or damaged teeth. A dentist may make adjustments to a tooth in order to create a bite in which all the teeth contact simultaneously when the jaws are in occluded condition. Determining a premature tooth contact, and information on tooth contact in general, such as a temporal sequence of tooth contacts and time intervals between tooth contacts, may be useful by dentists in creating an ideal bite condition.

One common approach to detect premature tooth contact may involve using a thin film of marking paper, such as a carbon paper, a special dye impregnated paper, or a wax paper, placed between an upper arch and a lower arch so that the biting surfaces of the teeth engage the inserted material during biting and leave some visible mark or indentation. This method may not be very reliable in indicating as to which tooth makes contact with an opposing tooth first, and it may also be difficult for a patient biting on the marking paper to pinpoint a location where the first contact may be occurring. Often a dentist may have to resort to trial and error techniques to grind a little portion at one supposed location of first contact, ask the patient to bite on the marking paper, and then again grind a little at another supposed location of contact hoping to bring occlusal equilibrium after a couple of grindings. An additional issue with using marking paper is that when marking paper is placed between the teeth, it may slightly affect the bite by its thickness. Typical thin marking papers are about eight microns thick and this thickness may be sufficient to leave a tooth eight microns higher than adjacent teeth during biting, constituting a clinically significant difference in many instances.

Embodiments of the present invention relate generally to the fields of dentistry and orthodontics, and more particularly to a structure and method of visualizing and analyzing tooth contact properties when upper and lower arches in a mouth are in a closed or occluded condition. Embodiments of the present invention provide an improved method and apparatus for detecting premature tooth contacts and for acquiring additional information relating to the engagement of teeth during biting. Embodiments use a thin flexible pressure sensing device determine a sequence in which occlusal contacts occur, and pressure magnitudes of such occlusal contacts, when upper and lower arches in a mouth are in an occluded condition. Embodiments also display the sequence and the pressure magnitudes of the occlusal contacts on a display device. This information may be advantageous in evaluating and treating an unstable bite to bring occlusal equilibrium.

In one embodiment, the pressure sensing device may include a thin film element that is deformable and compressible by mechanical pressure resulting from engagement of teeth during biting. In one embodiment, the pressure sensing device may comprise a transparent thin elastic film of carbon nanotube bundles that are approximately perpendicularly placed. The carbon nanotube bundles may be capable of sensing mechanical pressure resulting from the engagement of teeth during biting. In one embodiment, the pressure sensing device may include a pixel based pressure sensor. See e.g. Takei, K. et al. Nanowire active-matrix circuitry for low-voltage macroscale artificial skin. Nat. Mater. 9, 821-826 (2010). Embodiments may include pressure and tooth contact timing information being communicated to a processor, which in turn may display a graphical representation of a chronological sequence of tooth contacts relative to one another, and pressure magnitudes of the tooth contacts on a display device.

Embodiments of the present invention may also use augmented reality techniques well known in the art to overlay the graphical representation on an image of corresponding teeth in a jaw, on the display device. The display may indicate which part of which tooth is making first contact as well as pressure magnitudes of each tooth contact. Embodiments may also recommend adjustment of a tooth properties to alter one or both of sensing properties including a sequence of a first tooth contact relative to at least a second tooth contact, and pressure magnitudes of the first tooth contact and the second tooth contact. An adjusted tooth property may include, for example, a height, width, or length. In an example, the recommended adjustment may be based on a pressure threshold.

Embodiments may record history for each of sensing property variables and as a size of accumulated and archived data grows, embodiments may make enhanced recommendations by analyzing the data to provide tips to a dentist on improving efficiency of a procedure. Recorded sensing property variables may include, for example, a time for a procedure, one or more pressures of a tooth contact, a change in one or more pressures of a tooth contact over time, which tool is used to reduce the one or more pressures of a tooth contact, etc. These recommendations may provide a dentist with options that match the dentist's style (for example, if data indicates that the procedure is taking longer than ideal, recommendation may be for the dentist to move to a more aggressive dental tool, or for the dentist to remove more material during each instance of tooth material removal). Embodiments may also provide the dentist with subsequent feedback on effectiveness of new adjustments incorporated by the dentist based on recommendations made by the embodiments. Embodiments may also suggest an optimum duration for a given patient's bite sensing based on biting style of that patient (for example, if a patient bites consistently, the sensing data generated for analysis may be better as opposed to inconsistent bites or inconsistent bite alignments, for example, when a small child bites, that may result in a longer period of sensing needed to ensure an adequate recommendation). Biting consistency may be determined by, for example, comparing pressure data from a first bite and one or more second bites. Embodiments may also warn a dentist to reduce aggressiveness of tooth material removal and may also suggest collection of additional data points, when circumstances warrant it.

When describing the inventive structures and methods, the following terms have the following meanings, unless otherwise indicated.

As used herein a "nanostructure" is an object having at least one dimension between molecular and microscopic (micrometer-sized) dimension.

"Nanotube" as used herein is meant to denote one form of nanostructure having an aspect ratio of length to width greater than 10. The term "nanotube" includes single wall and multi-wall nanotubes unless specifically specified as distinct. In one embodiment, a carbon nanotube is at least one graphene layer wrapped into a cylinder. In one embodiment, a single wall carbon nanotube is a graphene rolled up into a seamless cylinder with diameter of the order of a nanometer. A multi-wall carbon nanotube is a plurality of graphene sheets rolled up into a seamless cylinder with diameter of the order of a nanometer.

"Electrical contact" means the electrically conductive connection from the plurality of electrically interconnected nanotubes and nanotube bundles to the circuit from which electrical properties are measured.

"Electrically interconnected" as used in conjunction with nanostructures means an electrically conductive pathway that is composed of at least two nanostructures that are engaged in electrical communication.

"Junction" with respect to nanostructures, e.g., nanotubes and nanotube bundles, means a point at which two nanostructures can transfer electrical charge from a first nanostructure to a second nanostructure in a plurality of electrically interconnected nanostructures.

"Electrically conductive", "electrical communication", and/or "electrically communicating" as used through the present disclosure means a material having a room temperature conductivity of greater than $10^{-8}$ $(\Omega\text{-m})^{-1}$.

A "matrix" is a medium between nanostructures that may be composed of a gas, liquid or solid.

The term "augmented reality" or "AR" refers to a physical real-world environment with elements augmented by computer-generated imagery enhancing the perception of reality. AR allows for the physical world and computer-generated content to be concurrently viewed. One example of AR is the yellow "first down line" seen on TVs while watching a professional or college football game. The augmentation may be in real-time, and may include user interactivity with the assistance of technology such as computer vision, head-mounted display, virtual retinal display, object recognition, sensors, and actuators. Non-limiting examples of display, tracking devices, and input devices include computer vision, image recognition, video tracking, edge detection software and hardware. The images of the physical environment may be detected by an image capture device. Non-limiting examples of an image capture device include a webcam, digital camera, digital camcorder, phone built into a cell phone or other PDA type device.

Embodiments of the present invention are described in detail below with reference to FIGS. 1-4.

Referring now to FIG. 1, a top view of a pressure sensing device 100 ("device 100") placed on an upper surface of teeth of a lower arch 103 of a mouth to enable sensing a chronological sequence and pressure magnitudes of tooth contacts is shown. The device 100 may illustrate one embodiment of the pressure sensing device used in sensing the chronological sequence and pressure magnitudes of teeth contacts between an upper arch 101 and a lower arch 103. It should be noted that it is by no means essential that the shape of the pressure sensing device 100 be as shown in FIG. 1, although this is a very convenient shape which lends itself readily to mass production, but may be varied in accordance with the outline of jaws into appropriate oval or curved shapes, as will be discussed with reference to FIG. 3 below.

The top face of the device 100 being displayed will be the face used against the teeth in the upper arch 101 for which the impression is to be taken while the opposing face of the device 100 will be used against the opposing teeth of the lower arch 103.

In one embodiment, the device 100 may include a rectangular left strip 107 and a rectangular right strip 109, both connected at one of their short sides to a rectangular center strip 105, as shown in FIG. 1. The device 100 may also include two registers 111 extending from the center strip 105, as shown in FIG. 1. The registers 111 may assist in proper alignment of the device 100 to teeth of the lower arch 103. Each of the registers 111 may have a rectangular cross-section and shaped to fit within a crevice between a set of front teeth of the lower arch 103. The registers 111 may have a thickness of between approximately 0.1 millimeter and approximately 2 millimeters. After the device 100 is reinserted in the proper position in the patient's mouth with each of the registers 111 making contact with a predefined tooth on the lower arch 103, the patient may be instructed to bite on the device 100 in normal occlusion.

In one embodiment, the left strip 107 and the right strip 109, and optionally the center strip 105, may comprise a material that is easily deformable by mechanical pressure resulting from opposing teeth biting into the device 100 in normal occlusion. In one embodiment, the device 100 material may comprise a transparent thin elastic film of one or more layers of approximately perpendicularly placed carbon nanotube bundles, as will be described in further detail with reference in FIG. 2.

Figure 2:
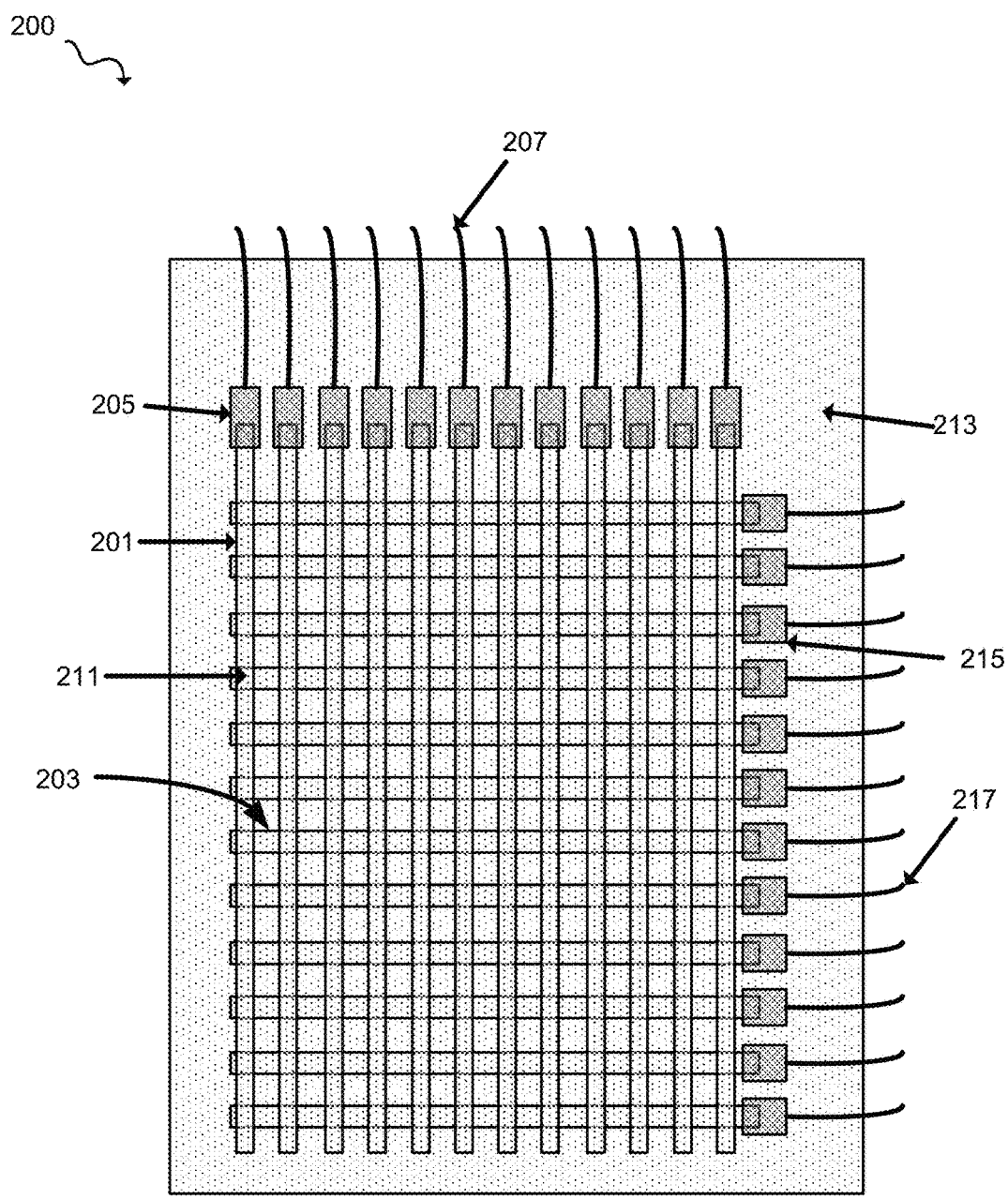
FIG. 2 illustrates a high resolution top view of the pressure sensing device, according to an embodiment of the invention.

Referring now to FIG. 2, structure 200 depicts a high resolution top view of a portion of device 100, in one embodiment. The structure 200 depicts a flexible transparent membrane composed of an array of vertical bundles 201 that include vertically aligned carbon nanotubes and an array of horizontal bundles 203 that include horizontally aligned carbon nanotubes, the horizontal bundles 203 being approximately perpendicular to the vertical bundles 201, with the vertical bundles 201 making contact with the horizontal bundles 203 at junctions 211. In one embodiment, the structure 200 may be composed of one or more layers of arrays of such vertical bundles 201 and the horizontal bundles 203.

In one embodiment, the vertical bundles 201 and the horizontal bundles 203 may be supported by a transparent and flexible substrate 213. In one embodiment, the substrate 213 may be composed of polydimethylsiloxane (PDMS) matrix. The arrays of carbon nanotube bundles embedded in the PDMS matrix may be structurally flexible and may be able to provide repeated sensing operations due to the high elasticities of both the PDMS matrix and the carbon nanotubes in the bundles. In one embodiment, the PDMS matrix may also include one or more organic field effect transistors and one or more thin film capacitors embedded therein. The organic field effect transistors and the thin film capacitors may be in electrical contact with the vertical bundles 201 and the horizontal bundles 203.

In one embodiment, at least one end of each of the vertical bundles 201 may be connected to a vertical electrical contact 205 which in turn may, in turn, be connected to a power source (not shown) and a processor (not shown) via a vertical line 207. Similarly, at least one end of each of the horizontal bundles 203 may be connected to a horizontal electrical contact 215 which in turn may, in turn, be connected to the power source and the processor via a horizontal line 217. In one embodiment, the nanotube bundles may be connected to the power source through one or more field effect transistors and/or one or more thin film capacitors. The power source may provide a substantially constant current to the plurality of carbon nanotubes in the vertical bundles 201 and the horizontal bundles 203, wherein the resistance, inductance and/or capacitance of each carbon nanotube contained therein may be correlated to pressure applied to it. Current from the current source may flow along a vertical bundle 201 and hop to another horizontal bundle 203 at a junction 211 between the bundles. The processor may receive output signals associated with sensing properties resulting from the pressure applied to the vertical bundles 201 and the horizontal bundles.

In one embodiment, when one or more sets of teeth are pressed against each other with the structure 200 material present between the teeth, each set including a first tooth located on the upper arch of a mouth and a second tooth located on a lower arch of the mouth which contact one another at a biting surface, the vertical bundles 201 and the horizontal bundles 203 may get compressed. The deformation of the vertical bundles 201 and the horizontal bundles 203 may alter electrical properties such as resistance, capacitance and/or impedance of the carbon nanotubes in the bundle. In one embodiment where the number of junctions between carbon nanotubes and nanotube bundles may not be fixed, application of pressure may increase the number of junctions thereby providing for an increase in the number of electrical pathways by which current may travel through the electrically interconnected carbon nanotubes and nanotube bundles. This may have the effect of altering electrical properties of the nanotube arrays in the vertical bundles 201 and the horizontal bundles 203. For example, this may reduce electrical resistance in vertical bundles 201 and the horizontal bundles 203. Changes in electrical properties of the carbon nanotubes resulting from tooth contacts may be received at the vertical electrical contacts 205 and the horizontal electrical contacts 215.

The electrical contacts may transmit these changes in electrical properties as output signals to the processor via the vertical lines 207 and the horizontal lines 217. The processor may thus be in communication with vertical bundles 201 and the horizontal bundles 203 via the vertical electrical contacts 205 and the horizontal electrical contacts 215 respectively. The processor may process the received output signals to provide information concerning tooth contact. For example, information concerning a tooth which makes contacts first during an occlusal closing may be determined, a sequence of contacts by various teeth may be determined, and time intervals between contacts of various teeth, among others, may be received and processed by the processor. In one example, the processor may process the received output signals to pinpoint one or more locations of the sensed pressure on the device 100, as well as pressure magnitudes of the sensed pressure, in addition to others, to be referred to hereinafter as "sensing properties". In one embodiment, the interpreted sensing properties may include a sequence of a first tooth contact relative to subsequent tooth contacts, and pressure magnitude of the first tooth contact and the subsequent tooth contacts, in addition to others.

In one embodiment, the processor may process the sensing properties for display on a display device in a variety of forms. For example, sequence of contacts by teeth during an occlusal closing of a mouth may be processed for display on a display device. The tooth contact data may be presented in other ways such as, for example, the percentage of time each tooth is contacted first, second and third during a plurality of occlusal closings. In one embodiment, an average of the results of a plurality of taps of a patient's jaw, indicating tooth contact associated with the taps, may be provided. In one embodiment, a percentage of time each tooth is contacted first, second and third during a plurality of taps may be displayed. In one embodiment, a graphical display of a tooth containing an arch may be provided with sensing properties information overlaid to indicate which tooth contacted first, and the order of contact of several teeth in an augmented reality set-up. In one embodiment, the display may include various colorings or shadings to indicate pressure magnitudes of each tooth contact. In one embodiment, the processer may save a history of the sensing properties in a storage device for subsequent use and/or for review by a dentist.

In one embodiment, the structure 200 material that forms part of the pressure sensing device 100 (FIG. 1) may able to measure any pressure, so long as the pressure does not diminish the structural integrity of the device 100. In one embodiment, the structure 200 may be capable of measuring pressures less than the minimum pressure that can be sensed by human fingers, which is on the order of approximately 20 $g/cm^2$. For example, the structure 200 may measure pressure values as low as 5 $g/cm^2$. It is noted that the above described dimensions and pressures are provided for illustrative purposes only, since the range of pressures being measured by the structures described above may be modified by increasing or decreasing the dimensions separating the adjacent vertical bundles 201 and horizontal bundles 203.

The structure 200 material may facilitate in performing a plurality of readings of tooth contacts inside a mouth, by the pressure sensing device 100 placed inside the mouth, during a period of time and determining sensing properties of the tooth contacts, based on the plurality of readings, wherein the sensing properties include one or more of: sequence of a first tooth contact relative to at least a second tooth contact, and pressure magnitude of the first tooth contact. The plurality of readings may be based on readings from some or all of mandible teeth and some or all of maxillary teeth within a person's mouth. The pressure sensing device 100 may be configured for placement between an upper and a lower jaw of a mouth, conforming one face of the device 100 to an occlusal surface of a first tooth, and conforming another face of the pressure sensing device to occlusal surface of the opposing second tooth.

Figure 3:
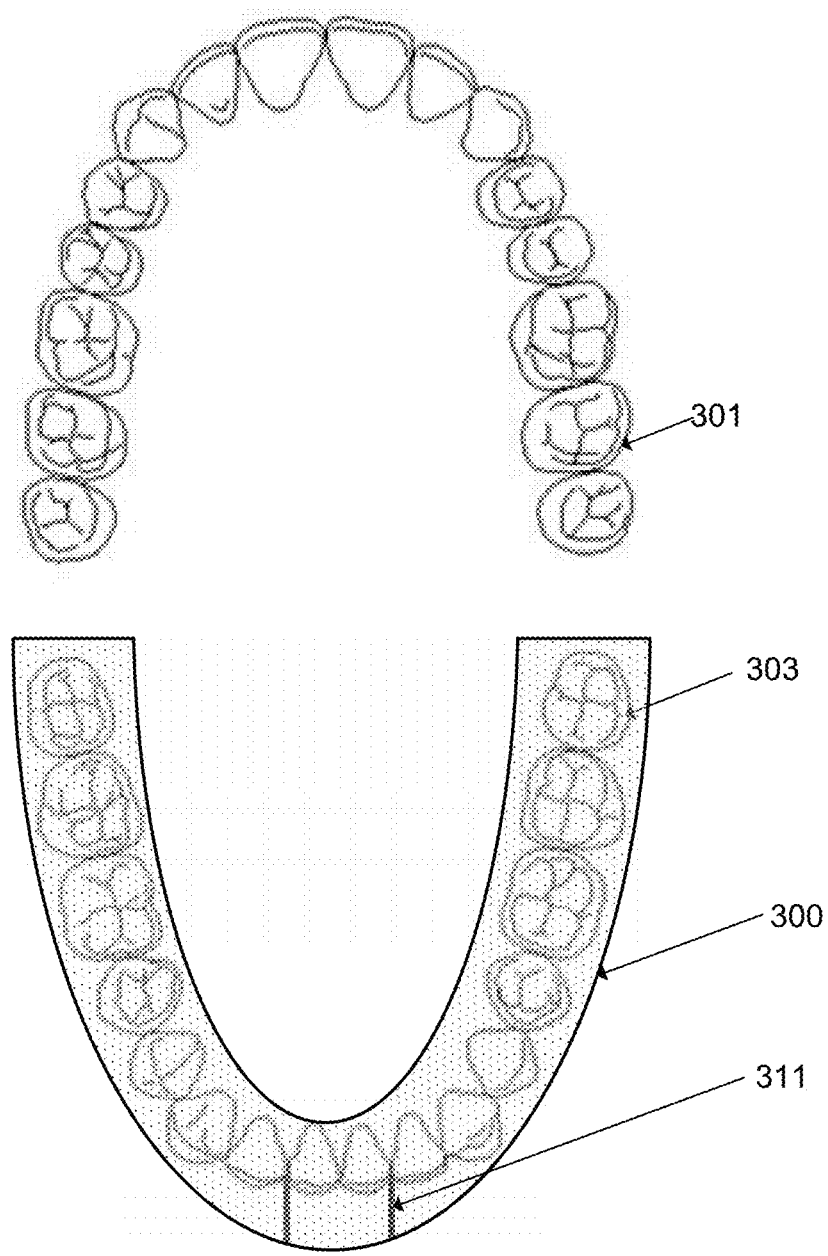
FIG. 3 illustrates a plan view of an alternate embodiment of the pressure sensing device placed on teeth of the lower arch of the mouth, according to an embodiment of the invention.

Referring now to FIG. 3, a top view of a pressure sensing device 300 ("device 300") placed on an upper surface of teeth of a lower arch 103 of a mouth to enable sensing a chronological sequence and pressure magnitudes of tooth contacts is shown. The device 300 may illustrate an alternate embodiment of the pressure sensing device used in sensing the chronological sequence and pressure magnitudes of teeth contacts between an upper arch 301 and a lower arch 303. Device 300 may have an arched shape, with the arched shape being configured to be positioned proximate to the occlusal surface of a user's dental arch. The shape and size of the device 300 can be varied to accommodate the size and number of teeth of which a bite and/or impression is to be taken. The top face of the device 300 being displayed will be the face used against the teeth in the upper arch 301 for which the impression is to be taken while the opposing face of the device 300 will be used against the opposing teeth of the lower arch 303.

In one embodiment, the device 300 may also include two registers 311 extending from a center portion of the device 300, as shown in FIG. 3. The registers 311 may assist in proper alignment of the device 300 to the teeth of the lower arch 303. Each of the registers 311 may have a rectangular cross-section and shaped to fit within a crevice between a set of front teeth of the lower arch 303. A space between the registers 311 may vary to accommodate individuals with differently sized teeth. The registers 311 may have a thickness of between approximately 0.1 millimeter and approximately 2 millimeters. After the device 300 is reinserted in the proper position in a patient's mouth with the each of the registers 311 making contact with a predefined tooth on the lower arch 303, the patient may be instructed to bite on the device 300 in normal occlusion.

In one embodiment, the device 300 material may comprise a transparent thin elastic film of one or more layers of perpendicularly placed carbon nanotube bundle arrays, similar to what was described with reference in FIG. 2.

In an embodiment, the device 300 may be reusable and cleanable using conventional cleaning techniques, such as, for example autoclaving. In another embodiment, the device 300 may be reusable and require a sanitary covering, such as, for example, a thing plastic film. In another embodiment, the device 300 may be disposable.

Figure 4:
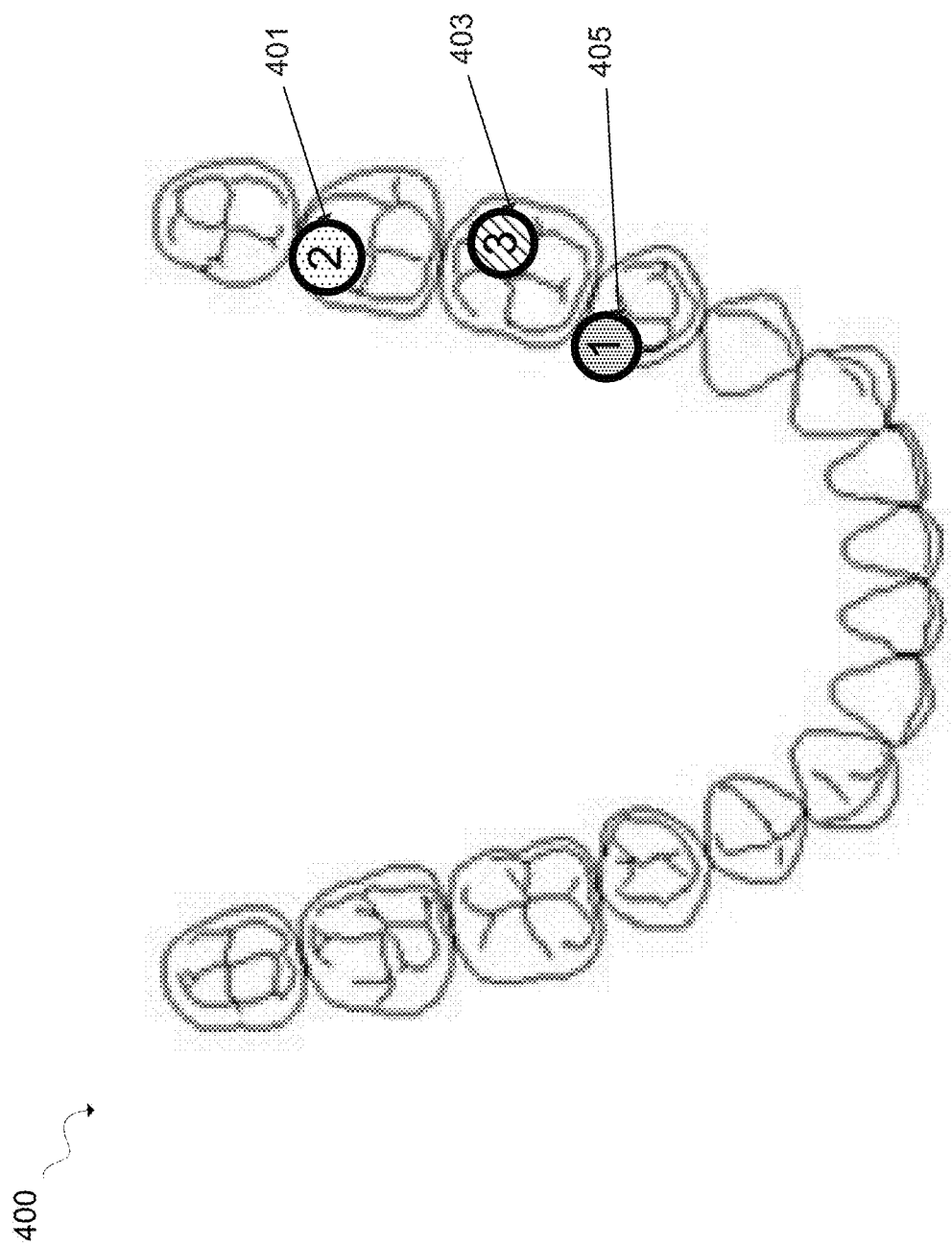
FIG. 4 illustrates a display of a chronological sequence and pressure magnitudes of tooth contacts as displayed on a display device, according to an embodiment of the invention.

Referring to FIG. 4, structure 400 depicts a display, on a display device, of a graphical representation of one or more of: a chronological sequence of the tooth contacts relative to one another; and the pressure magnitudes of the tooth contacts. In one embodiment, the processor receiving output signals from the vertical bundles 201 and the horizontal bundles 203 (FIG. 2) of device 100 (FIG. 1), may process the signals into a visual display depicting a chronological sequence and pressure magnitudes of each of the tooth contacts on a visual display device.

In one embodiment, various colors or patterns may be utilized to depict different pressure magnitude ranges or bands of tooth contacts. As an illustrative example, in FIG. 4, each point of occlusal or tooth contact with device 100 placed between the upper and lower arches may be indicated on a visual display by a circle by the processor, such as, for example, circles 401, 403, and 405. In an embodiment, a pattern in circle 401 may indicate a highest pressure magnitude band, a pattern in circle 403 may indicate a moderate pressure magnitude band, and a pattern in circle 405 may indicate a low pressure magnitude band. It should be noted that more than three pressure magnitude bands may be utilized to display the sensing properties. In addition, in one embodiment, a sequential number may be assigned by the processor to each point of occlusal contact depending on a chronological sequence in which the occlusal contacts may have occurred during an occlusal closing of teeth of an upper arch and a lower arch. As an illustrative example, in FIG. 4, circle 405 has number "1" to indicate a location of first tooth contact, circle 401 has number "2" to indicate a location of second tooth contact, circle 403 has number "3" to indicate a location of third tooth contact. In an embodiment, additional visual and/or textual information may be presents, such as, for example, a numerical display of a pressure at a tooth contact, topographical tooth information, or any combination thereof. In an embodiment, a zoom feature may allow a user to enlarge a selected portion of the image.

The visual display may be, for example, a monitor, lenses on glasses, a projection on a surface, or any combination thereof. The visual display may be controlled by, for example, a mouse, keyboard, touch pad, touch screen, voice directed interface, eye movement directed interface, or any combination thereof.

In one embodiment the processor, to which pressure and contact timing information of tooth contacts may be communicated from the device 100, may form part of a control system (not shown). The control system may also include a display device which is operable to visually indicate a display of the sensing properties associated with the tooth contacts. In one embodiment, the display device may represent a computer monitor. In one embodiment, the control system may also include peripheral devices such as, for example, printers to provide a tangible copy of the sensing properties, and storage devices to store a digital copy of the sensing properties. In one embodiment, the control system may include known augmented reality techniques to superimpose the sensing properties data over an image of the lower arch or upper arch being viewed through a wearable display device such as, for example, Google® Glass. In one embodiment, occlusal contact between upper and lower teeth of a patient when the upper and lower arches are in an occluded condition may be displayed on a user interface in an interactive set-up.

The device 100 may be enclosed in a liquid impermeable sterilizable housing so that the device may be sterilized and reused following the evaluation of the bite of a particular patient.

Figure 5:
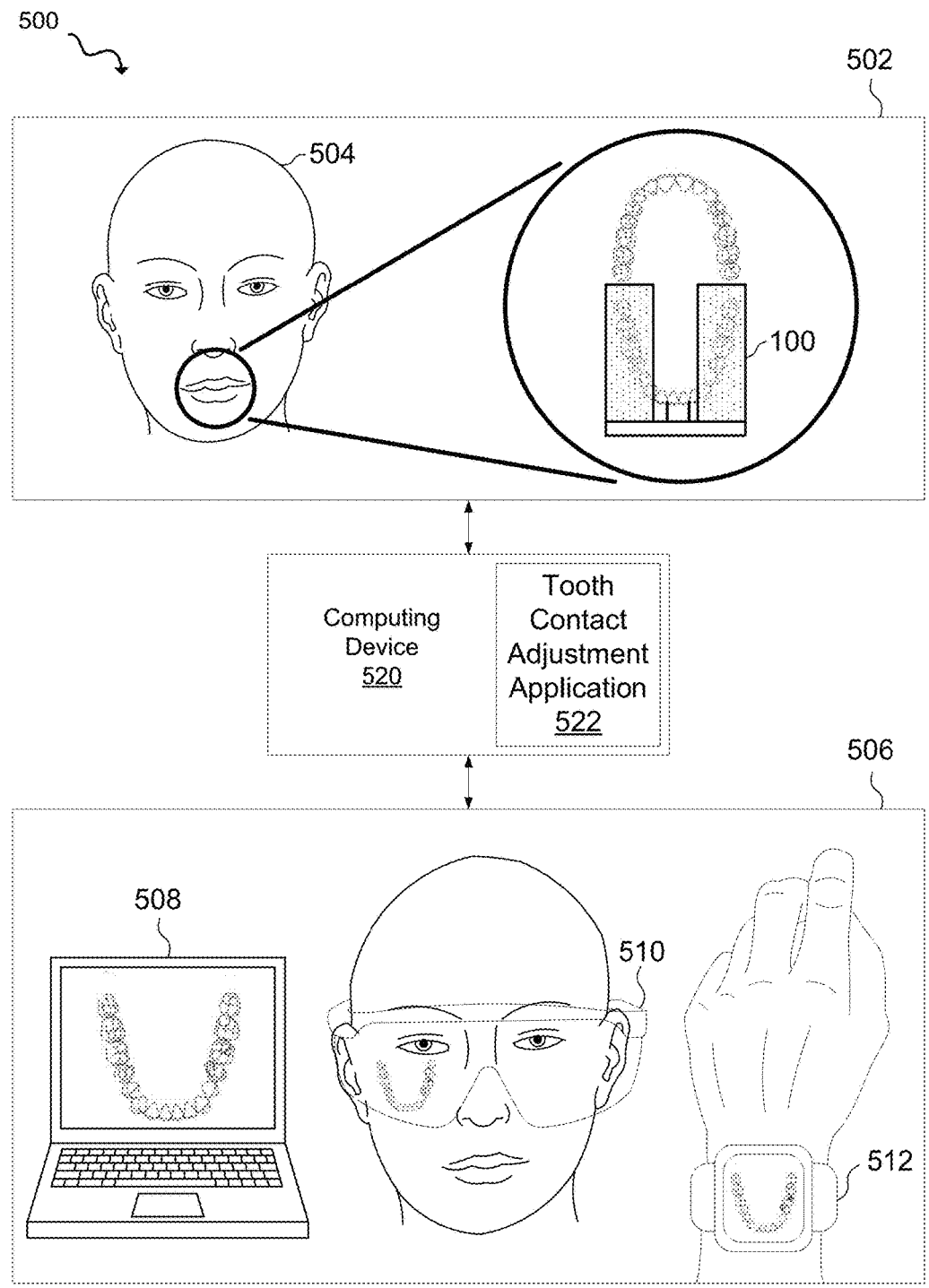
FIG. 5 illustrates a tooth contact adjustment system, according to an embodiment of the invention.

Referring to FIG. 5, a tooth contact adjustment system 500, according to an embodiment of the invention, is shown. The tooth contact adjustment system 500 may include a tooth contact environment 502, a computing device 520, and a display device 506.

The tooth contact environment 502 may include a user 504 and a pressure sensing device. The user 504 may be a patient at a dental or orthodontist office. The pressure sensing device may be, for example, the pressure sensing device 100, the pressure sensing device 300, or any combination thereof.

The computing device 520 may be may be a laptop computer, tablet computer, netbook computer, personal computer (PC), desktop computer, phone, glasses, watch, or any programmable electronic device. Computing device 520 may include internal and external hardware components, as depicted and described in further detail with respect to FIG. 7. Computing device 520 includes a tooth contact adjustment application 522.

The display device 506 may be any display device known in the art. For example, the display device 506 may be a computer 508, glasses 510, watch 512, or any combination thereof. In a preferred embodiment, the display device may be the glasses 510. The glasses 510 may be worn by an operator (e.g. a dentist or orthodontist) while performing a tooth contact adjustment. The glasses 510 may allow the operator to visualize tooth contact properties without requiring the operator to look away from the user 504 (e.g. the patient). In an embodiment, the glasses 510 may superimpose a visual representation of the tooth contact properties in a line of site of the operator. Thus, when the operator looks at the teeth of the user 506, the operator may see the visual representation of the tooth contact properties on the teeth of the user 506. The computing device 520 and the display device 506 may be the same device or a different device. In a preferred embodiment, the computing device 520 and the display device 506 may be the same device.

The tooth contact system 500 may involve performing one or more readings of tooth contacts using the pressure sensor device (e.g. the pressure sensing device 100 or the pressure sensing device 300). In an embodiment, the one or more readings of tooth contacts may generate one or more data sets. The computing device 520 may use the one or more data sets may to determine sensing properties of the tooth contacts. Textual and/or visual information regarding the sensing properties of the tooth contacts may be generated by the computing device 520. The generated textual and/or visual information may include, for example, a topographical representation of teeth of the user 504, symbols identifying one or more high pressure areas, numerical representation of one or more pressures associated with one or more areas, or any combination thereof. The generated textual and/or visual information may be transmitted to a display device 506. The display device 506 may present the generated textual and/or visual information to the operator (e.g. a dentist or orthodontist). The display device 506 may be the glasses 510 worn by the operator. The operator may use information presented on the display device 506 to determine where a tooth adjustment is needed. The operator may make an adjustment to one or more teeth. The process may be repeated by again performing one or more readings of tooth contacts using the pressure sensor device. Information presented on the display device 506 may show an operator how a tooth adjustment has affected one or more teeth of the user 504.

Figure 6:
FIG. 6 illustrates a flow chart for a tooth contact adjustment method, according to an embodiment of the invention.
Figure 6:

Referring now to FIG. 6, a tooth contact adjustment method 600, according to an embodiment of the invention, is shown. The tooth contact adjustment method 600 may include performing a plurality of readings of tooth contacts 604, determining sensing properties of the tooth contacts 608, and displaying a visual representation of the sensing properties of the tooth contacts 616.

Performing a plurality of readings of tooth contacts 604 may be performed by the pressure sensing device (e.g. the pressure sensing device 100 or the pressure sensing device 300). The pressure sensing device may be placed inside the mouth of a user 504 (FIG. 5). The plurality of readings may be performed over a period of time. The time period may range from, for example, nanoseconds to hours, and ranges therebetween. The pressure sensing device may be configured for placement between an upper and a lower jaw of a mouth, conforming one face of the pressure sensing device to an occlusal surface of a first tooth, and conforming another face of the pressure sensing device to occlusal surface of the opposing second tooth. The plurality of readings may be based on readings from some or all of mandible teeth and some or all of maxillary teeth within a person's mouth.

Determining sensing properties of the tooth contacts 608 may be performed by the computing device 520 (FIG. 5). Determining sensing properties of the tooth contacts 608 may be based on the plurality of readings of tooth contacts. Sensing properties that may be determined include, for example, a sequence of a first tooth contact relative to at least a second tooth contact, a pressure magnitude of the first tooth contact, or any combination thereof. Determining sensing properties of the tooth contacts 608 may also include analyzing sensing properties of the tooth contacts. For example, the computing device 520 may analyze the sensing properties from one or more readings to provide the operator with one or more additional pieces of information, such as, for example, recommending adjustment of a tooth property to alter one or both of the sensing properties, providing information about the timing of the procedure, providing information about a change in a tooth property, or any combination thereof.

Figure 7:
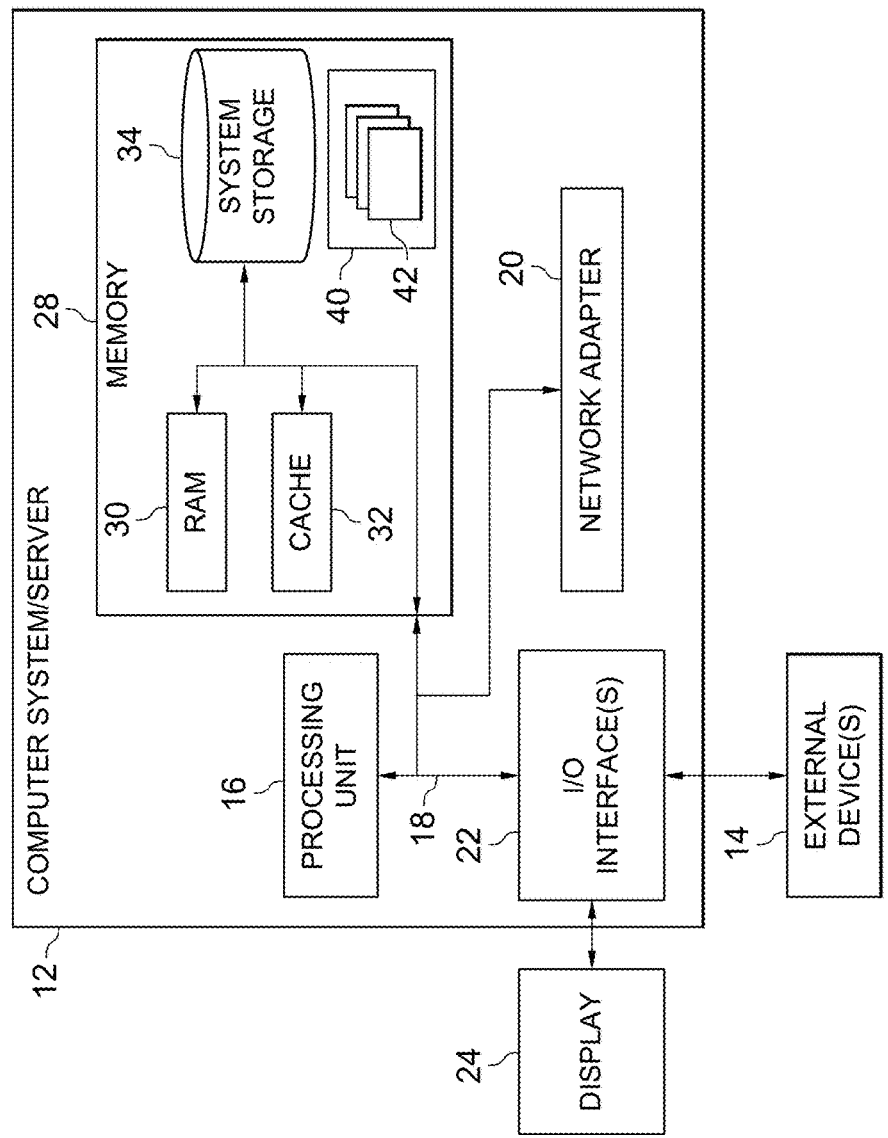
FIG. 7 illustrates a schematic of a computing node, according to an embodiment of the invention.

Referring now to FIG. 7, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Embodiments of the invention may provide a method and means for forming a completely accurate dental bite for a patient. In combination with a jaw trajectory apparatus, the tooth contact information may be correlated with jaw trajectory information to provide a more complete indication of stability of a patient's bite. The ability to sense and display occlusal contacts as described above may assist a dentist in planning treatment for a patient.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method of measuring tooth contact properties, the method comprising:

performing a plurality of readings of tooth contacts, by a pressure sensing device wherein the pressure sensing device comprises a plurality of nanostructures wherein at least a portion of a first nanostructure is perpendicularly placed relative to a portion of a second nanostructure; and determining sensing properties of the tooth contacts, based on the plurality of readings, wherein the sensing properties include a chronological sequence of contact made by the tooth contacts, a time interval between the chronological sequence of contact made by the tooth contacts, and a pressure magnitude of the tooth contacts.

2. The method of claim 1, further comprising:
displaying a graphical representation of results of the determining step of claim 1 on a display device.

3. The method of claim 1, further comprising:
displaying, on a display device, a graphical representation of one or more of:
the chronological sequence of contact made by the tooth contacts relative to one another;
the time interval between the chronological sequence of contact made by the tooth contacts; and
the pressure magnitude of the tooth contacts.

4. The method of claim 3, wherein the displaying further comprises:
overlaying the graphical representation on an image of corresponding teeth in a jaw, on the display device.

5. The method of claim 4, wherein the displaying further comprises:
overlaying the graphical representation on the display device in alignment with a line of site of one or more teeth, wherein the display device is glasses.

6. The method of claim 1, further comprising:
recommending adjustment of a tooth property to alter one or more of the sensing properties.

7. The method of claim 1, wherein the pressure sensing device comprises a transparent elastic film, wherein the transparent elastic film comprises carbon nanotubes.

8. The method of claim 1, further comprising:
communicating with a computer system, by the pressure sensing device, wherein the step of determining the sensing properties of the tooth contacts is performed by the computer system.

9. The method of claim 1, wherein the plurality of readings are based on readings from some or all of mandible teeth and some or all of maxillary teeth within a person's mouth.

10. The method of claim 1, wherein the sensing properties further include a change in pressure magnitude of the tooth contacts over time.

* * * * *